(12) United States Patent
Wijnhoven et al.

(10) Patent No.: US 6,277,605 B1
(45) Date of Patent: Aug. 21, 2001

(54) ISOTHERMAL POLYMERASE CHAIN REACTION BY CYCLING THE CONCENTRATION OF DIVALENT METAL IONS

(75) Inventors: Michael Wijnhoven, Brugge; Rudi Rossau, Ekeren, both of (BE)

(73) Assignee: Innogenetics N.V. (BE)

( * ) Notice: Subject to any disclaimer, the term of this patent is extended or adjusted under 35 U.S.C. 154(b) by 0 days.

(21) Appl. No.: 09/194,661

(22) PCT Filed: Apr. 6, 1998

(86) PCT No.: PCT/EP98/01998
§ 371 Date: Dec. 4, 1998
§ 102(e) Date: Dec. 4, 1998

(87) PCT Pub. No.: WO98/45474
PCT Pub. Date: Oct. 15, 1998

(30) Foreign Application Priority Data

Apr. 4, 1997 (EP) .................................................. 97870046

(51) Int. Cl.[7] ............................... C12Q 1/68; C12P 19/34

(52) U.S. Cl. ........................... 435/91.2; 436/6; 436/91.1; 436/91.21

(58) Field of Search ........................... 435/6, 91.2, 91.21, 435/41, 810

(56) References Cited

U.S. PATENT DOCUMENTS 5,773,238 * 6/1998 Shukla ..................................... 435/41
6,033,850 * 3/2000 Purvis ...................................... 435/6

OTHER PUBLICATIONS

Perkin Elmer. Biotechnology Catalog (1992–1993), p. 26.*
Copy of XP 002039656, Eichhorn et al pp. 7323–7328 J. Am. Chem. Soc. vol. 90, 1968.

Blagoi Iup et al. Molekuliarnaia Biblogig (1978) 12(4): 795–805.

* cited by examiner

*Primary Examiner*—Carla J. Myers
*Assistant Examiner*—Alexander H. Spiegler
(74) *Attorney, Agent, or Firm*—Bierman, Muserlian and Lucas

(57) ABSTRACT

The present invention provides an alternative PCR amplification which does not draw upon the use of thermostable DNA polymerases. It provides means for the controlled manipulation of denaturing conditions which do not demand the use of high denaturing temperature. More particularly, it provides means for the controlled oscillation of divalent metal ions, preferably of divalent metal ions such as $Cu^{2+}$, $Zn^{2+}$, $Mn^{2+}$ and $Cd^{2+}$, which are known to destabilize the DNA helix and thereby decrease the melting temperature of the DNA helix. The invention also provides methods for the automatization of this process. For instance, by means of cathodic reduction of the divalent metal species the concentration can be decreased to levels that allows for reannealing of separated sands with the primers; while oxidation of deposited metals or oxidation of monovalent metal ions, can restore the initially high concentration that allows for separation of both strands that make up the DNA helix. Electrolytic control of metal ion activity hence provides a tool for the repetitive isothermal denaturation of duplex DNA, and consequently can be used as a substitute for thermal cycling in the amplification of genetic material. Isothermal denaturation of dsDNA may be of considerable importance in the biotechnology and biomedical industry. A key advantage of this method is that it opens perspectives for a wide range of DNA polymerases that can be used with this reaction.

11 Claims, 4 Drawing Sheets

Figure 1:
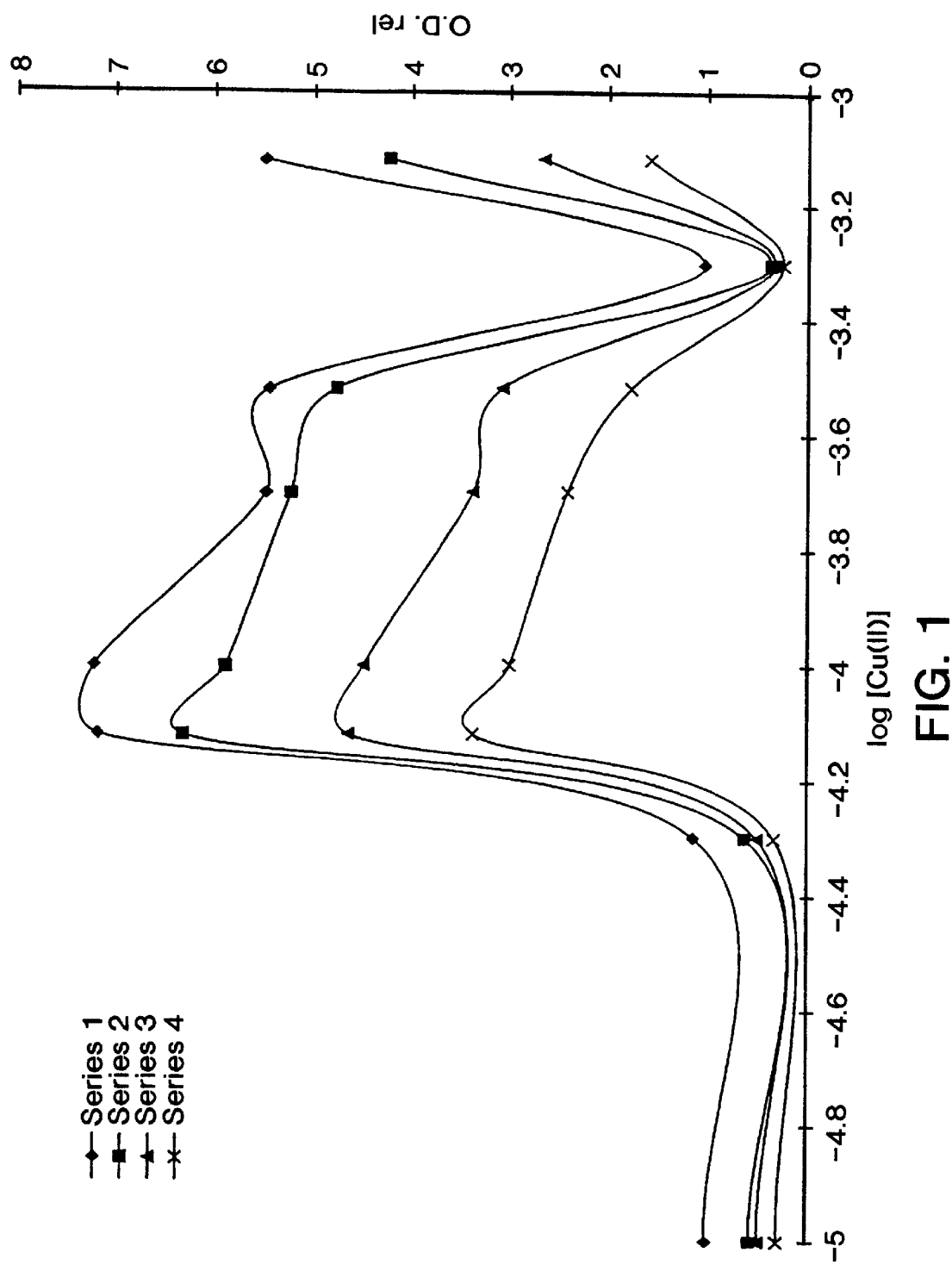

ISOTHERMAL POLYMERASE CHAIN REACTION BY CYCLING THE CONCENTRATION OF DIVALENT METAL IONS

This application is a 371 of PCT/EP98/01998 filed Apr. 6, 1998.

The present invention relates to a process for amplifying nucleic acid sequences by means of the polymerase chain reaction. More specifically, it relates to a process wherein the consecutive cycles of denaturation and renaturation are achieved by a controlled oscillation of the local concentration of divalent metal ions. This allows the reaction to proceed at constant temperature, and depending upon the metal ions used at lower temperatures near physiological values.

In the biotechnology and biomedical industry large number of copies of a particular gene or polynucleic acid may be needed for various purposes such as sequencing and diagnostic applications. Simple and reliable methods to generate such amounts are consequently indispensable for the success of future industrial and scientific developments Any new technique to amplify genetic material and in particular for diagnostic applications, should minimize human intervention and chemical addition steps. A further prerequisite is that it should be easily amenable to automation.

Currently relatively large amounts of particular gene sequence can be produced by the polymerase chain reaction (EP-B-0200 362, EP-B-0201 184). A method which offered significant benefits over classical procedures such as cloning. In essence PCR is based on the repetitive thermal denaturation of double stranded (dsDNA), a process which is known as thermal cycling. As the reaction temperature is cycled between about 70° C. and 94° C., the polymerases would denature soon. In Kieppe et al., *J. Mol. Biol.* 56:341 (1971), a process is described for synthesizing DNA using primer-initiated, template-directed repair replication, and it is suggested that cycles of replication could be repeated, adding every time a fresh dose of DNA polymerase, which would be an expensive procedure A nice solution was offered by the introduction of thermostable DNA polrmerases which were derived from thermophilic bacteria (e.g. *Thermus aquaticus*). Such enzymes, however, have a higher error rate than other Dolymerases, particularly of eukaryotic origin, which operate at lower temperatures.

The need for extreme conditions to allow separation of both strands that make up the DNA helix directly results from the fact that the DNA double helix is a relatively stable structure due to the propensity of the bases to form hydrogen bonds with each other in a very specific way. Apart from base pairing several additional conditions need to be satisfied to guarantee stability at a particular temperature. Ionic strength of the medium has a very important role and at low electrolyte concentration dsDNA is denatured due to the lack of counterions. These counterions may be mono- or divalent metal ions which stabilize the structure by binding to the phosphate moieties and effectively cancel the net negative charges preventing unwinding of the helix due to repulsive forces. However at elevated concentrations some divalent metal ions in particular: $Cu^{2+}$, $Cd^{2+}$, $Zn^{2+}$ and $Mn^{2+}$) destabilize the double helical structure. This is because all these ions exhibit an affinity to both phosphate and bases, with their association constants being significantly different, $Cu^{2+}$. for example has the highest affinity for DNA bases and in particular N-7 of guanine is the prime target for $Cu^{2+}$ complexation. Hence, when an increasing portion of the phosphata vacancies are filled, the affinity constant for the binding of a particular metal to phosphate decreases as a consequence of the cooperative binding nature. At this point, binding to the DNA bases becomes more important and competition for hydrogen bonding is initiated. The effect is manifested in a lowering of the melting temperature ($T_m$) of the dsDNA (Eichhorn and Shin, *J. Am. Chem. Soc.*, 90:7323 (1968); P-Y. Cheng, Biochem. Biophys. Acta., 102:314 (1962); Schreiber and Daune, Biopolymers, 8:130 (1969)).

The present invention provides alternative solutions for the above-mentioned problem. Instead of providing thermostabile DNA polymerases to cope with the extremely high temperatures needed to allow the DNA to denature, the present invention provides means for manipulating the conditions such that the DNA can denature at much lower temperatures and consequently no longer draws upon the use of thermostabile DNA polymerases.

It is thus an aim of the present invention to provide an alternative PCR amplification process.

It is also an aim of the present invention to provide an alternative PCR amplification process, that does not draw upon the use of thermostabile DNA polymerases.

It is also an aim of the present invention to provide an alternative type of PCR amplification kits.

It is further an aim of the present invention to provide an alternative type of PCR amplification device.

According to a preferred embodiment, the present invention relates to the use of a controlled oscillation of the concentration of divalent metal ions such as $Cu^{2+}$, $Cd^{2+}$, $Zn^{2+}$ and $Mn^{2+}$, thereby forming the basis for isothermal denaturation of the double helix.

The present invention also provides means for the automatization of this process. For instance, the new method favours dynamic electrochemical control of the activity of ionic species present. Furthermore only divalent metal ions are considered at this stage This however, by no means excludes the potential to extend electrolytic control to the activity of mono-valent cations, which are equally important members in terms of contributions to total ionic strength. The present invention departs from methods that allow separation of both strands of a DNA helix. This is not achieved solely by increasing the temperature but also by increasing the local concentration of divalent metal ions that have the tendency to destabilize the DNA helix Destabilization of the DNA helix is reflected in the lowering of the melting temperature ($T_m$) of DNA (i.e. the midpoint in the transition of dsDNA to ssDNA). $Cu^{2+}$, ions stabilize the double helical structure at low concentrations. However, at elevated concentrations $Cu^{2+}$ ions start to interfere with hydrogen bonding resulting in the transition from double helical into ssDNA.

According to a preferred embodiment the present invention relates to a process for amplifying at least part of a specific double-stranded nucleic acid sequence contained in a sample comprising:

(a) separating the nucleic acid strands in said sample essentially with a means for increasing the local concentration of metal ions, preferably of divalent metal ions;

(b) treating the strands with at least one oligonucleotide primer under hybridizing conditions essentially with a means for decreasing the local concentration of metal ions, preferably divalent metal ions, and in the presence of an inducing agent for polymerization and the different nucleotides, such that an extension product of the respective primer(s) is synthesized which is complementary to one end of the sequence to be amplified on one of the strands such that an extension product can be synthesized from said Drimer which, when it is separated from its complement, can serve as a template for synthesis of an extension product of the other primer;

(c) separating the primer extension products from the templates on which they were synthesized to produce single-stranded molecules essentially with a means for increasing the local concentration of metal ions, preferably divalent metal ions;

(d) treating the single-stranded molecules generated from step (c) with the primers of step (b) under hybridizing conditions essentially with a means for decreasing the local concentration of metal ions, preferably divalent metal ions, and in the presence of an inducing agent for polymerisation and the different nucleotides such that a primer extension product is synthesized using each of the single-strands produced in step (c) as a template; and, if desired;

(e) repeating steps (c) and (d) at least once; whereby the amount of the sequence to be amplified increases exponentially relative to the number of steps in which primer extension products are synthesized The term "essentially" refers to the fact that the nucleic acid strand separation and annealing process according to the present invention is mainly brought about by cycling or fluctuating the metal ion concentrations. This does exclude the influence and concomitant use of other agents and/or parameters for the described process. The term "separating" has to be interpreted in a broad sense, such that it does not only refer to the actual physical separation of both strands that make up a DNA helix or a template-primer complex, but more to the physical separation of the DNA bases that interact as within a Watson Crick DNA-duplex. In its broadest sense the term "separation" of two strands can be defined operationally as a process which creates a situation, such that annealing of another primer or an oligonucleic acid becomes possible to one o: the original strands that made up the original DNA-duplex.

The term primer as used throughout the specification and the claims has to be interpreted in a broad sense A primer as used in ordinary PCR reactions is usually about basepairs long. However, with respect to the present invention a primer can be much shorter, and many more primers can be used as the usual pair of primers used in an ordinary PCR reaction. Also these primers can be immobilized and/or labelled, such that detection becomes possible. The term primer does not implicate that this oliqonucleic acid has to be used in a process in which the primer is extended in a polymerase reaction wherein the complementary strand is used as a template. In this respect the term primer can be more properly defined as an ordinary oligonucleotide.

Besides polymerase chain reactions to amplify DNA, the essential teachings of the present invention, however, also may be applied to other types of reactions involving repetitive denaturation of genetic material. An example of such a reaction is: denaturation of a DNA-duplex according to the methods of the present invention, and concomitant or subsequent annealing according to the methods of the present invention, of a primer or a primer pair or many primers or oligonucleic acids of any type including the use of PNA's.

The present invention more particularly relates to a nucleic acid amplification process that allows for the controlled cycling of other metal ions than $Cu^{2+}$. While $Mg^{2+}$. does not readily bind with the bases of the nucleotides that make up the polynucleic acid polymer, thereby interfering with the hydrogen bonding, other bivalent metal ions like $Cu^{2+}$, $Cd^{2+}$, $Zn^{2+}$ and $Mn^{2+}$, do exhibit this property, and thus are candidate ions that can be used to substitute for $Cu^{2+}$. It has to be understood that certain combinations of divalent metal ions are equally well candidates to lower the melting temperature of the DNA helix. By way of example but not limiting for the present invention, a useful combination could be to allow fluctuations of the $Cu^{2+}$ concentration or of the concentrations of $Cd^{2+}$, $Zn^{2+}$ and $Mn^{2+}$, or to allow fluctuations of the concentrations of combinations of such divalent metal ions (such as $Cu^{2+}$ and $Cd^{2+}$, or $Cu^{2+}$ and $Zn^{2+}$, or $Cu^{2+}$ and $Mn^{2+}$, while the $Mg^{2+}$ concentration is allowed to fluctuate in reverse sense (see Examples section). This can be helpful in order to destabilize the DNA helix, because $Mg^{2+}$-ions are known to stabilize the DNA helix. It is also helpful to allow reannealing or renaturation of the DNA helix, or of a primer with a template, because higher $Mg^{2+}$ concentrations facilitate dissociation of the DNA-ion complex and thus the reversibility of the process.

The concentrations of divalent metal ions used according to the present invention will vary typically from $10^{-2}M$ to $10^{-5}M$, more preferably from $10^{-3}M$ to $10^{-4}M$.

According to another embodiment, the present invention also relates to the use of a controlled oscillation of the concentration of $Mg^{2+}$ ions. Although this process is not based on competition between metal ion and hydrogen bonding and unwinding of dsDNA is solely based on the counter ion effect, it has significant advantages in terms of toxicity to DNA polymerase enzymes that may be used. In this case the temperature for unwinding of the DNA helix unfortunately needs to be relatively high (about 70° C.). This however may be improved by exerting control over the monovalent metal ions present in the reaction medium, or by adding small amounts of divalent cations such as $Cu^{2+}$, $Cd^{2+}$, $Zn^{2+}$ and $Mn^{2+}$, or by increasing the hydrophobicity of the reaction medium.

The present invention also relates to analogous processes for amplifying single stranded nucleic acids using primers in which the primers are annealed to the nucleic acid by means of metal ion concentration fluctuations as described above and below.

In case $Cu^{2+}$ is used as a divalent metal ion, the $Cu^{2+}$ concentration that is initially high to allow strand separation of the DNA helix, can be decreased electrochemically in a controlled way through selective reduction. This can be achieved at relatively high current efficiency as the standard reduction potential of $Cu^{2+}$ and $Mg^{2+}$ are separated by about 2.7V. The metal copper that has been deposited on the cathode can be oxidized again towards $Cu^{2+}$, thereby increasing the $Cu^{2+}$ concentration to the initial concentration that allows separation of the DNA strands. Successive oxido-reduction cycles of copper, hence provides a means for the cycling process needed for a polymerase chain reaction, namely the successive separation of both strands of the DNA helix and reannealing with appropriate primers, upon which the primers can be extended by using the separated strands from the previous cycle as a template.

The present invention relates to the use of any type of electrode that allows for reduction of $Cu^{2+}$ or other divalent metal ions as mentioned above. Such process can include the use of a conventional electrolytic cell consisting of a dropping mercury or a rotating disc electrode to establish the kinetics appropriate for the reaction.

The present invention also relates to the use of specific types of electrodes that allow for the selective reduction of $Cu^{2°}$ or other divalent metal ions as mentioned above, that can be constructed and that can possibly be based on information obtained from the above mentioned electrode. Such electrodes can be based on known technologies such as semi-conductor technology such as ITSET (Ion Selective Field Effect Transistor). A further advantage of electrochemical reduction is that it provides cheap active monitoring system to follow the reaction as electrical signals are generated from the electrode as a reaction product.

A very convenient method to control the concentration of metal ions is by cathodic reduction of the desired ionic species. This does not exclude the possibility that the $Cu^{2+}$, concentration that was initially high, is restored by adding $Cu^{2+}$, ions as a substitution for the oxidation of metal CuO towards $Cu^{2+}$.

The present invention also relates to the use of chelating agents (e.g. EDTA) in combination with the above mentioned process. It is anticipated that metal chelators can be employed in order to facilitate diffusion to the cathode and/or dissociation of the copper-DNA complex.

The present invention also relates to a process wherein the above mentioned methods are combined with the successive oxido-reduction of monovalent metal ions, possibly the monovalent metal ions of the above mentioned ions, possibly in combination with chelators known in the art that may be specific for the above mentioned ions.

According to a preferred embodiment, the present invention also relates to the use of several regimens to bring about a cycling of successive denaturation and renaturation of the DNA, wherein several combinations of metal ions, preferably divalent and as mentioned above, possibly in concert with chelators.

By way of example (see Examples section below) but not limiting for the present invention are two regimens, one wherein the $Mg^{2+}$ concentration is kept constant and one with variable $Mg^{2+}$ concentration. Constant high $Mg^{2+}$ concentration limits the binding vacancies for any incoming metal ion to the base pairs as phosphates are saturated, this reduces the concentration of metal needed and consequently speeds up the oxido-reduction cycles. Apart from this, toxic effects due to the metal ions with respect to the polymerase enzymes are kept to a minimum. In those cases where the stabilizing effect of $Mg^{2+}$ outweighs the destabilization by the respective metal ions, a regimen wherein a cycling magnesium concentration is used might be preferred. In each case, contributions from monovalent metal ions to the stability of duplex DNA should be as low as possible.

According to another preferred embodiment, the present invention also relates to alternative ways to allow for a controlled oscillation of the local metal ion concentration. One possibility is the use of a dialysis system, wherein the polymerase chain reaction components are kept contained from the surrounding medium through a dialysis membrane, and wherein the surrounding medium can be flushed with appropriate solutions, in a cyclic and controlled way, thereby allowing fast exchange of electrolytes, chelators and metal ions between the solutions that are flushing the sealed off system and the solution in which the components for the polymerase chain reaction are contained. Such a procedure allows for the controlled oscillation of the concentration of many compounds. By way of example but not limiting to the present invention, it is anticipated that it might be advantageous to manipulate the concentration of the electrolyte as well.

The present invention also relates to a process for nucleic acid amplification wherein the agent for polymerization is a DNA polymerase which can function at temperatures near physiological values.

The following examples merely serve to illustrate some of the aspects of the present invention. The contents of all mentioned references and patents (particularly all patents relating to PCR) are to be considered as incorporated within the content of the invention.

EXAMPLES

Example 1

Annealing of Primers to DNA Treated with Cu(II)

1.1. Materials & Methods

To demonstrate the annealing of a primer to a target DNA sequence upon denaturation of the double helical structure by cupric ions, primers are incubated with DNA at various Cu(II) concentrations. Following quenching of the reaction with EDTA, the products are transferred to micro wells and captured through the biotin-streptavidin system the DNA is a PCR product which is biotinylated at one end through the inclusion of a biotin-labelled primer in the PCR reaction) The incorporation of a digoxigenin label to the added primer provides a quantitative assay when coupled to the anti-dig-alkaline phosphatase conjugate and incubation with substrate.

1.1.1. Chemicals

All chemicals were analytical grade (e.g. Merck) or better and used without further purification. Copper(II) stock solutions (0.1 M) were prepared volumetrically and the dilutions used in the experiments were stored at 4° C, new dilutions were made on a weekly basis. Oligonucleotides both labelled and unlabelled were purchased from Eurogentech (Belgium). Anti-dig alkaline phosphatase was obtained from Boehringer-Mannheim. Other reagents used were components of the inno-Lipa or inno-Test systems.

1.1.2. Dna

Complementary target DNA is prepared by amplifying the HLA class II type DRB fragment using generic primers DRB p5' (2) 5'-bio and DRB p3' (4) through a PCR reaction which yields a 280 bp. PCR product biotinylated at one end. Non complementary DNA involves the amplification of a HLA class I fragment type B fragment using the primers Pin 1 and P2-bio originating in a 500 bp. PCR product. The amplification of the correct fragments is verified by agarose gel electrophoresis and ethidium bromide staining. Subsequently the PCR products are purified using a Qiagen Quiaquick PCR product purification kit, and eluted in distilled water (pH 7.5).

1.1.3. Preparation of microtitre wells

Nunc immuno module Maxisorp microwell strips are coated overnight with streptavidin diluted in carbonate buffer pH 9.6 (5 $\mu$g ml$^{-1}$, 250 ng well). Following incubation the wells are blocked (PBS/Casein 0.5%/KCG) for 2 hours oat room temperature. After washing with inno-Lipa rinse solution and biotin capture buffer, 75 $\mu$l biotin capture buffer (Na$_2$HPO$_4$ 20 mM, NaCl 150 mM, 0.1 % Tween 20, pH 7.5) is added. Subsequently the experimental solutions (experiments were performed in micro- PCR tubes) are transferred to the microwells and left for 90 minutes at 37° C. After coupling the wells are rinsed and incubated for 30 minutes at room temperature with anti-dig alkaline phosphatase conjugate (diluted 1/5000 in inno-Lipa conjugate diluent) The wells are now rigorously washed and incubated with the alkaline phosphatase substrate (paranitrophenyl phosphate 2 mg. ml$^{-1}$ in 100 mM Tris-HCl, 100 mM NaCl, 5 mM MgCl$_2$, pH 9.7). Optical density (O.D) readings (405–595 nm) are obtained at regular time intervals on a micro plate reader (in this case a Bio-tek EL-312e biokinetics reader). The values are then expressed as relative optical density (O.D rel) which is the ratio of copper containing over non copper containing experimental solutions the background absorption (i.e. the optical density of the substrate solution) is subtracted from both values.

1.1.4. Experimental solutions

A typical experiment involves the annealing of a primer to a target sequence as a function of cupric ion concentration.

The reaction mixture is made up in the following way: target DNA (final concentration 1–2. $10^{-5}$ M DNA-Phosphate), primer 1 m and if necessary other nucleic acid components (e.g. dNTP's) are added together, following this salt solution of desired ionic strength is added and finally the various copper dilutions ($Cu(NO_3)_2$ or $CuSO_4$) are added. The mixture is then incubated at a given temperature (e.g. 42° C.) for 30 minutes and when completed the reaction is quenched with EDTA ($Na_4$) (The final concentration of EDTA should be at least equal to the highest copper concentration). The reaction is left for a further 15 minutes at 42° C. and then rapidly quenched on ice. The contents are now transferred to the micro wells containing the biotin capture buffer and the steps as outlined above are followed.

1.2. Annealing and Intraspecific Competitive Annealing (FIG. 1)

Conditions: DNA 280 bp. PCR product $1.2\times10^{-5}$ M DNA-Phosphate, NaCl 5 mM, Primer digoxigenin labelled DRB p3' (4) 1 $\mu$M (1 mM primer corresponds to $2\times10^{-5}$ M DNA-Phosphate), Primer DRB p3' (4) unlabelled: Series 1, 0 $\mu$M; Series 2, 1 $\mu$M; Series 3, 2 $\mu$M; Series 4, 3 $\mu$M, Cu $(NO_3)_2$ variable. O.D. rel represents relative optical density mean values for triplicate experiments.

The results which are summarized in FIG. 1, clearly show that there exists an annealing maxima (Series 1) at an optimal cupric ion concentration which is between 0.075 and 0.1 mM $Cu(NO_3)_2$. This roughly corresponds to a copper to DNA-Phosphate ratio of 2/1. If the copper mediated annealing of a primer is sequence specific, it is expected that an identical but unlabelled primer would compete with the labelled primer for DNA binding sites. If this is the case a decrease in relative O.D. values as a function of unlabelled primer concentration would indicate that such process is indeed occurring. The gradual depression of the peaks corresponding with series 2, 3 and 4, hence provides evidence for intraspecific competition between primers for a annealing site on the DNA template.

Figure 2:
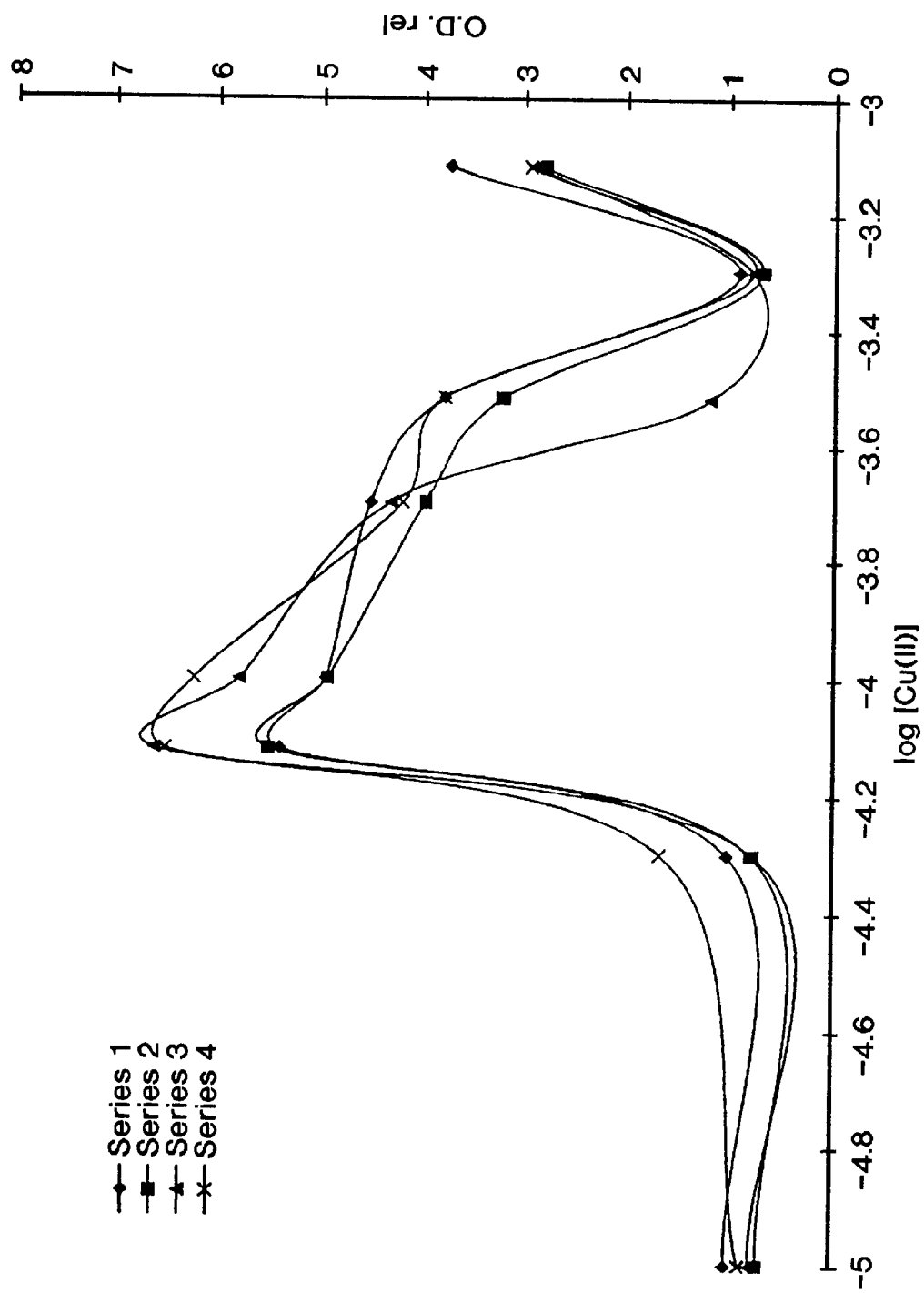

1.3. Annealing and Interspecific Competitive Annealing (FIG. 2)

Conditions: DNA 280 bp. PCR product $1.2\times10^{-5}$ DNA-Phosphate, NaCl 5 mM, Primer digoxigenin labelled DRB p3' (4) 1 $\mu$M, Primer non complementary unlabelled: Series 1, 0 $\mu$M; Series 2, 1 $\mu$M; Series 3, 2 $\mu$M; Series 4, 3 $\mu$M, $Cu(NO_3)_2$ variable OD. rel represents relative optical density mean values for triplicate experiments.

As in FIG. 1 a relative annealing maximum is observed at the same cupric ion concentration This time however the highest peak does not correspond with series 1 (i.e. when only labelled primer is present) indicating there is no competition for the DNA binding site. In more formal terms this means there is no niche overlap between the two competing primer species, and together with FIG. 1 provides conclusive evidence for copper mediated sequence specific primer annealing at an optimum cupric ion concentration. Actually the peak associated with series 1 has the lowest value, this may be a coincidence however a more fundamental reason for this behaviour implicates the nature of copper induced DNA (a B-helix is assumed throughout) denaturation, which may be different from the one brought about by heat or alkali. Higher relative optical density values in the presence of nucleic acid analogues such as non complementary primers (which is the case for series 2, 3 and 4) are expected when the denaturation of B-DNA brought about by copper ions is only partial or involves a profound structural change which allows the formation of DNA-primer complex through a triple-helix with the primers engaged in correct Watson-Crick base pairing. In both cases the presence of nucleotide analogues would interfere with the reannealing of the double helix through the zippering reaction which is likely to remove annealed primers, as such the kinetics of the zippering is slowed down in series 2, 3 and 4 and higher relative optical density values are obtained.

Figure 3:
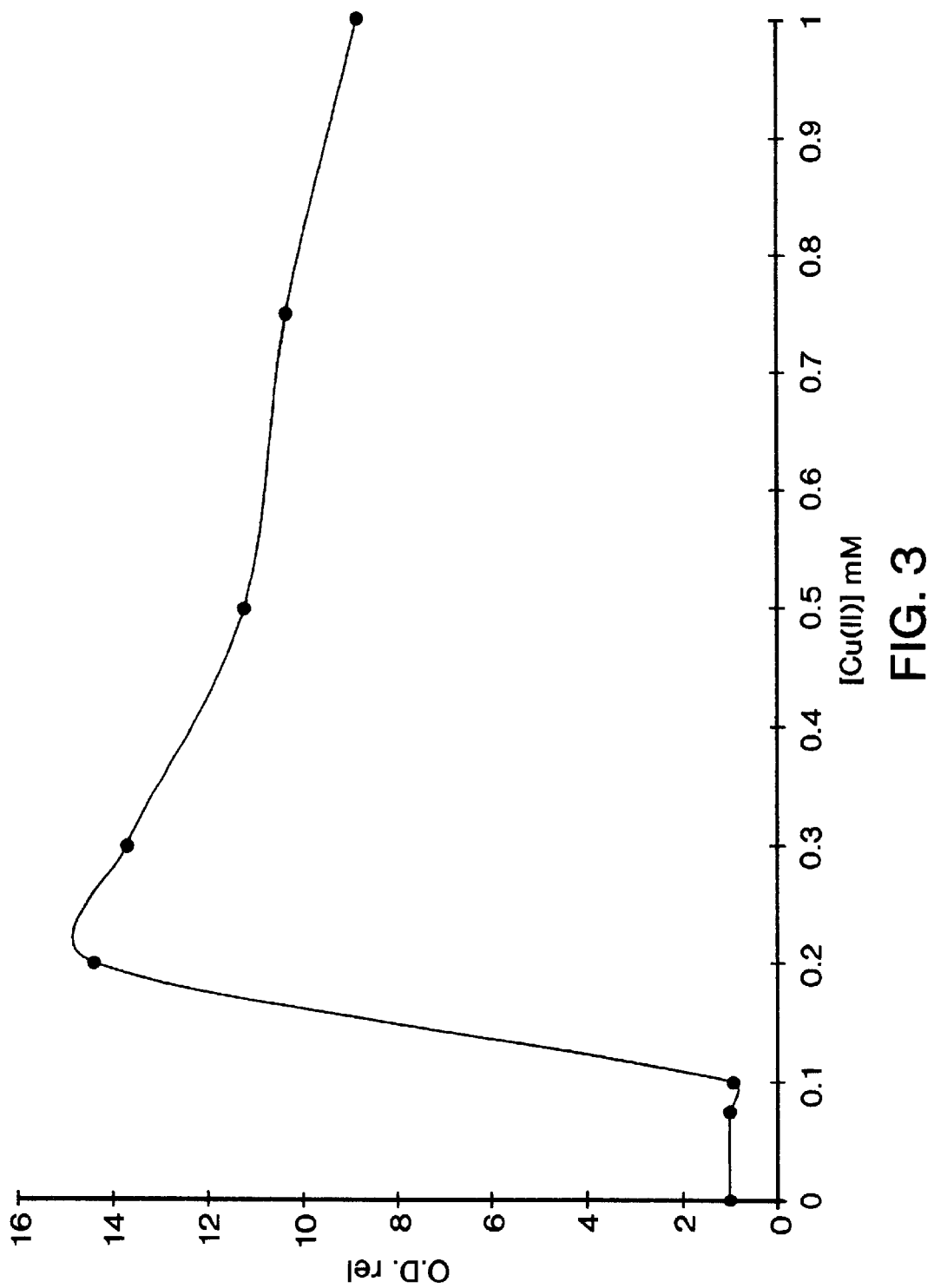

1.4. Annealing in Presence of Deoxyribonucleotide Triphosphates (dNTP's) (FIG. 3)

Conditions DNA 280 bp. PCR product $1.2\times10^{-5}$ M DNA-Phosphate, Primer digoxigenin labelled DRBp3' (4) 1 $\mu$M, dNTP's (equal amounts of dGTP, dCTP, dATP and dTTP, supplied as tetralithium salts) 0.2 mM, NaCl 1 mM, Cut $(NO_3)_2$ variable concentration. Relative optical density is calculated from mean values of duplicate experiments.

The shift of the annealing peak to a $Cut(NO_3)_2$ concentration of 0.2 mM is not surprising as the total nucleotide base and phosphate concentration to which cupric ions bind is now much higher through the addition of dNTP's. Striking however is that the relative optical density value is doubled when compared to FIGS. 1 and 2. This further supports the idea that copper induced annealing proceeds through a different mechanism when compared to the annealing of primers to single stranded DNA generated by conventional denaturation (e.g. heat or alkali). Another feature of the curve generated in FIG. 3 is a broader annealing plateau following the peak. This indicates that a further advantage of adding dNTP's to the reaction mixture is that the cupric ion buffering capacity of the medium is increased, and annealing proceeds over a broader cupric ion concentration. As dNTP's are a necessary component of the amplification mixture of a polymerase reaction, this experiment shows that amplification through copper mediated annealing by cycling the cupric ion concentration is indeed a realistic option.

Figure 4:
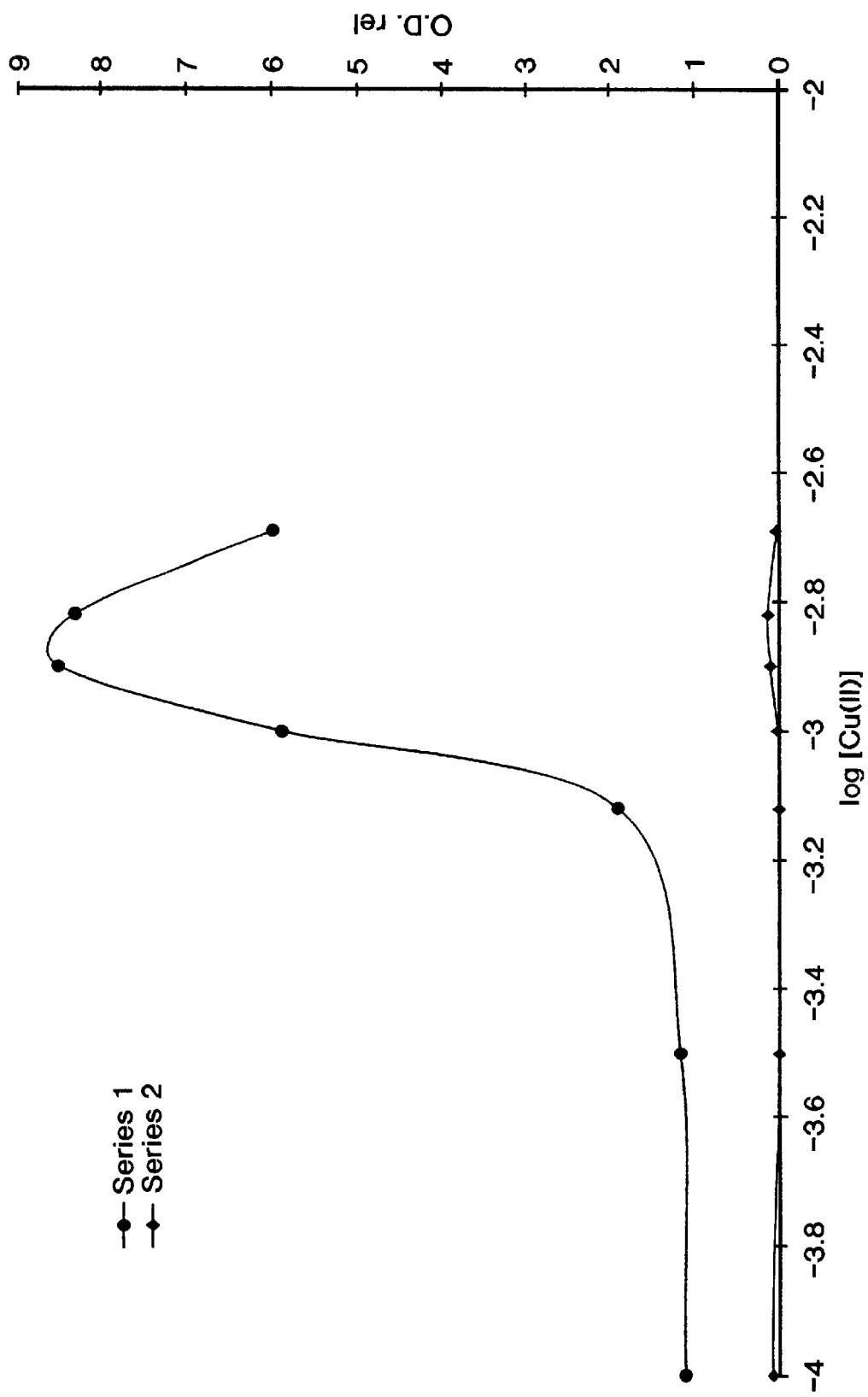

1.5. Annealing in Presence of dNTP's and $MgCl_2$, at 42° C. (FIG. 4)

Conditions: Series 1, complementary DNA 280 bp. PCR product $1.2\times10^{-5}$ M DNA-Phosphate, Series 2, non-complementary DNA 500 bp. PCR product, both series are incubated with: Primer digoxigenin labelled DRB D3' (4) 1 $\mu$M, dNTP's (equal amounts of each) 0.8 mM, $MgCl_2$ 1 mM, $Cu(NO_3)_2$ variable concentrations. Relative optical density is calculated from mean values of duplicate experiments.

In series 1 again a shift of the annealing peak is noticed with a maximum at 1.25 mM $Cu(NO_3)_2$, both the higher dNTP concentration and the presence of $MgCl_2$ are responsible for this behaviour. However there is no indication that the annealing becomes non specific even at this rather elevated cupric ion concentrations (series 2). Previously it was found (results not shown) that increasing ionic strength inhibited the copper mediated annealing of primers. At about 50 mM NaCl the annealing is completely quenched, and when $Mg^{2+}$, ions are added this effect is even more pronounced and cannot be explained in terms of ionic strength as at 1 mM $MgCl_2$ the annealing of a primer is already inhibited reaching only half the maximum value obtained in 5 mM NaCl and this at more elevated cupric ion concentrations (0.75 mM). The high affinity binding of $Mg^{2+}$ ions to the DNA phosphate groups which results in an increasing stability of the double helical structure is believed to be the cause of this behaviour With magnesium ions bound to the DNA phosphate groups cupric ions are hindered from binding to the DNA bases and as such destabilization of the DNA double helical structure becomes less probable. However binding of magnesium to DNA-phosphates is a anticooperative process and the association constant decreases as a function of $Mg^{2+}$ ions already bound to the DNA When dNTP's are present $Mg^{2+}$ ions bind to the DNTP phosphate groups in a non cooperative manner that is the association constant does not change. The overall effect is a dramatic decrease in the free magnesium ion concentration, and hence a lower coverage of DNA phosphate groups with magnesium ions. Considering the binding of copper(II) ions to the DNA bases this is essentially a cooperative process once nucleation has been achieved, whereas binding of cupric ions to the dNTP's is a non cooperative process. Hence the role of dNTP's as bifunctional metal ion buffer now becomes quite apparent, and is a valuable tool for the optimalization of an amplification medium.

Example 2

Cycling Shemes

Several schemes of controlled conditions for performing amplification processes according to the present invention are set out below. In each of the below mentioned cases contributions from monovalent metal ions to the stability of duplex DNA should be as low as possible.

The time scale to bring about the desired changes in metal ion concentration (typically from $10^{-2}$M to $10^{-5}$M) is of the order of a few seconds, depending upon electrode design and the metal species under consideration Considering the action of $Cu^{2+}$, $Zn^{2+}$, $Cd^{2+}$ and $Mn^{2+}$ at least two possible strategies for each metal ion emerge. All reactions described below are polymerase chain reactions to amplify DNA; this however does not exclude the utility of a the essential teachings of each of the following examples in other reactions involving repetitive denaturation of genetic material.

2.1. Schemne with Variable [$Mg^{2+}$]

Although this method is not based on competition between metal and hydrogen bonding and unwinding of dsDNA is solely based on the counter ion effect, it has significant advantages in terms of the toxicity DNA polymerase enzymes that may be used. The reaction temperature unfortunately needs to be relatively high (about 75° C.), or the primer concentration should be high, or the relative cycling times prolonged. This however may be improved by exerting control over the monovalent metal ions present in the reaction medium. All metals in each of the following cases are supplied as chlorides.

The following steps are distinguished in the PCR process according to the present scheme:

1. Add sample dsDNA to low [$Mg^{2+}$]
2. Add primers (excess concentration) and increase [$Mg^{2+}$]
3. Add polymerase and dNTP's (excess concentration)
4. After completion, reduce magnesium by electrolysis and repeat step 2

It should be noted that primers, dNTP's and polymerase may be present throughout the reaction.

2.2. Scheme using Variable [$Cu^{2+}$] and Constant [$Mg^{2+}$]

In this scheme using relatively high constant magnesium concentration, minimal levels of $Cu^{2+}$ are needed to unwind DNA. Reaction temperatures can be as low as 40° C. or less. The following steps are distinguished in this scheme:

1. Add sample dsDNA at high [$Cu^{2+}$]
2. Add primers (excess concentration) and reduce $Cu^{2+}$
3. Add polymerase and dNTP's (excess concentration)
4. After completion, oxidize copper from the working electrode and repeat steps 2 and 4 as many times as required It should be noted that Drimers, dNTP's and polymerase may be present throughout the reaction.

2.3. Scheme using Variable [$Cu^{2+}$] and Variable [$MG^{2+}$]

If the stabilizing effect of $Mg^{2+}$ prevents $Cu^{2+}$ ions from unwinding the duplex DNA. magnesium concentration needs to be actively regulated throughout the reaction. This complicates the electrode system to be used. However, standard reduction potentials for copper and magnesium are sufficiently separated to allow for a high current efficiency at least with respect to those two ions. The magnesium concentration only needs to be as high as is required by the replication system used. Reaction temperatures could be as low as 40° C. The following steps of the PCR reaction may be distinguished according to this scheme:

Add sample dsDNA at high [$Cu^{2+}$] and low [$Mg^{2+}$]

2. Add primers (excess concentration), reduce $Cu^{2+}$ and oxidize $Mg^{2+}$
3. Add polymerase and dNTP's (excess concentration)
4. After completion oxidize $Cu^{2+}$ and reduce $Mg^{2+}$, repeat step 2 and 4 as many times as required.

It should be noted that primers, dNTP's and polymerase may be present throughout the reaction.

2.4. Scheme using Variable [$Zn^{2+}$] and Constant [$Mg^{2+}$]

The same principle as for (B) is applied here. The reaction temperature, however, is about 75° C. Furthermore zinc ions can be used in normal thermal cycling at concentrations of approximately $10^{-4}$M, to decrease the upper limit cycling temperature to about 75° C. Problems involving toxicity with zinc are considerably reduced as $Zn^{2+}$ is a natural component of most replication systems in vivo. The Following steps are distinguished in a PCR reaction according to this scheme:

1. Add sample dsDNA at high [$Zn^{2+}$]
2. Add primers (excess concentration) and reduce $Zn^{2+}$
3. Add polymerase and dNTP's (excess concentration)
4. After completion, oxidize zinc from the working electrode and repeat step 2 and 4 as many times as required.

It should be noted that primers, dNTP's and polyrmerase may be present throughout the reaction.

2.5. Scheme using Variable [$Zn^{2+}$] and variable [$Mg^{2+}$]

The same principle as for © is applied, the reaction temperature is around 75° C. The following steps are distinguished in a PCR reaction according to this scheme:

1. Add sample dsDNA at high [$Zn^{2+}$] and low [$Mg^{2+}$]
2. Add primers (excess concentration), reduce $Zn^{2+}$ and oxidize $Mg^{2+}$
3. Add polymerase and dNTP's (excess concentration)
4. After completion oxidize $Zn^{2+}$ and reduce $Mg^{2+}$, repeat step 2

It should be noted that primers, dNT's and polymerases may be present throughout the reaction.

2.6. Scheme using Variable [$Mn^{2+}$] and constant [$Mg^{2+}$]

The same principle as for (B) is applied, with a reaction temperature of approximately 75° C. When using $Mn^{2+}$ several problems should be taken into account. Manganese can be used as a substitute or magnesium requirement during DNA replication. However the rate or replication is increased significantly and a higher level of error incorporation is to be expected. This may have serious draw-backs if up to 60 cycles are performed. Furthermore in presence of manganese most polymerases are unable to distinguish between dNTP's and rNTP's and so both are incorporated during chain elongation.

1. Add sample dsDNA at high [$Mn^{2+}$]
2. Add primers (excess concentration), reduce $Mn^{2+}$
3. Add polymerase and dNTP's (excess concentration)
4. After completion oxidize $Mn^{2+}$, repeat step 2 and 4 as many times as required It should be noted that primers, dNTP's and polymerases may be present throughout the reaction.

2.7. Scheme using Variable [$Mn^{2+}$] and variable [$Mg^{2+}$]

The same principle as for © is applied, the reaction temperature is about 75° C. The following steps are distinguished in a PCR reaction according to this scheme.

1. Add sample dsDNA at high [$Mn^{2+}$] and low [$Mg^{2+}$]
2. Add primers (excess concentration), reduce $Mn^{2+}$ and oxidize $Mg^{2+}$
3. Add polymerase and dNTP's (excess concentration)
4. Following completion oxidize $Mn^{2+}$ and reduce $Mg^{2+}$, repeat step 2 and 4 as many times as required It should be noted that primers, dNTP's and polymerases may be present throughout the reaction.

2.8. Scheme using Variable [$Cd^{2+}$] and constant [$Mg^{2+}$]

The same principle as for (B) is applied, the reaction temperature is about 60° C. Cadmium is a notorious pollutant heavy metal, so only if $Cd^{2+}$ based denaturation compares favourably with the above methods it may be considered as an option. The following steps are distinguished in a PCR reaction according to this scheme.

1. Add sample dsDNA at high [$Cd^{2+}$]
2. Add primers (excess concentration), reduce $Cd^{2+}$,
3. Add polymerase and dNTP's (excess concentration)
4. Following completion oxidize $Cd^{2+}$, repeat step 2 and 4 as many tiles as required.

It should be noted that primers, dNTP's and polymerases may be present throughout the reaction.

2.9. Scheme using Variable [$Cd^{2+}$] and variable [$Mg^{2+}$]

The same principle as for © is applied, the reaction temperature is about 60° C. The following steps are distinguished in a PCR reaction according to this scheme.

1. Add sample dsDNA at high [$Cd^{2+}$] and low [$Ng^{2+}$],
2. Add primers (excess concentration), reduce, $Cd^{2+}$ and oxidize $Mg^{2+}$
3. Add polymerase and dNTP's (excess concentration)
4. Following completion oxidize $Cd^{2+}$ and reduce $Mg^{2+}$, repeat step 2 and 4 as many times as required It should be noted that primers, dNTP's and polymerases may be present throughout the reaction.

What is claimed is:

1. A process for amplifying at least part of a specific double stranded nucleic acid sequence contained in a sample comprising:

(a) increasing the local metal ion concentration whereby the nucleic acid strands in said sample separate;

(b) decreasing the local metal ion concentration in the presence of at least one oligonucleotide primer, dNTP's and an agent that induces polymerization whereby said at least one primer anneals to the nucleic acid strands, and a primer extension product is synthesized which is complementary to one end of one of the strands of the nucleic acid sequence to be amplified;

(c) increasing the local metal ion concentration whereby the primer extension products in said sample separate from the nucleic acid strands on which they were synthesized to produce single stranded molecules;

(d) decreasing the local metal ion concentration in the presence of an agent that induces polymerization and dNTP's whereby the single-stranded molecules generated from step (c) anneal with the primers of step (b) and whereby a primer extension product is synthesized using each of the single strands produced in step (c) as a template;

wherein the steps for increasing or decreasing the local metal ion concentration are accomplished through dialysis.

2. The process in claim 1, further comprising;

(e) repeating steps (c) and (d) at least once; whereby the amount of the nucleic acid sequence is amplified exponentially.

3. The process of claim 1, wherein said metal ion is selected from the group consisting of $Cu^{2+}$, $Cd^{2+}$, $Zn^{2+}$, and $Mn^{2+}$.

4. The process of claim 1, wherein said step of increasing the local metal ion concentration further comprises oxidizing said metal ions to form monovalent or divalent metal ions.

5. The process of claim 1, wherein step of increasing the local metal ion concentration further comprises lowering the apparent concentration of an electrolyte present in said sample.

6. The process of claim 1, wherein said step of increasing the local metal ion concentration further comprises increasing the reaction temperature.

7. The process of claim 1, wherein said step (b) of decreasing the local metal ion concentration further comprises reducing said metal ions.

8. The process of claim 1, wherein said step of decreasing the local metal ion concentration further comprises increasing the apparent concentration of the electrolyte present in said sample.

9. The process of claim 1, wherein said step of decreasing the local metal ion concentration further comprises decreasing the reaction temperature.

10. The process of claim 1, wherein the metal ions are divalent metal ions.

11. The process of claim 10, wherein the divalent metal ion is magnesium.

* * * * *

UNITED STATES PATENT AND TRADEMARK OFFICE
CERTIFICATE OF CORRECTION

PATENT NO. : 6,277,605 B1
DATED : August 21, 2001
INVENTOR(S) : Wijnhoven et al.

It is certified that error appears in the above-identified patent and that said Letters Patent is hereby corrected as shown below:

Title page,
ABSTRACT, line 14, change "sands" to -- strands --.

Column 1,
Line 22, change "developments Any" to -- developments. Any --.
Line 40, change "procedure A" to -- procedure. A --.
Lines 41-42, change "polrmerases" to -- polymerases --.
Line 44, change "Dolymerases" to -- polymerases --.
Line 60, change "ions in" to -- ions (in --.
Line 64, change "$Cu^{2+}$. for" to -- $Cu^{2+}$ for --.

Column 2,
Line 43, change "helix Destabili-" to -- helix. Destabili- --.
Line 46, change "$Cu^{2+}$, ions" to -- $Cu^{2+}$ ions --.

Column 3,
Line 1, change "Drimer" to -- primer --.
Line 36, change "one o:" to -- one of --.
Line 39, change "sense A" to -- sense. A --.
Line 40, change "about basepairs" to -- about 20 basepairs --.
Line 46, change "oliqonucleic" to -- oligonucleic --.

Column 4,
Line 67, change "ITSET" to -- IFSET --.

Column 5,
Line 9, change "CuO" to $Cu^o$ --.

Column 6,
Line 10, change "system the" to -- system (the --.
Line 45, change "oat" to -- at --.
Line 57, change "(O.D)" to -- (O.D.) --.
Line 61, change "(O.D rel)" to -- (O.D. rel) --.
Line 62-63, change "solutions the" to -- solutions. The --.

UNITED STATES PATENT AND TRADEMARK OFFICE
CERTIFICATE OF CORRECTION

PATENT NO. : 6,277,605 B1
DATED : August 21, 2001
INVENTOR(S) : Wijnhoven et al.

It is certified that error appears in the above-identified patent and that said Letters Patent is hereby corrected as shown below:

Column 7,
Line 44, change "variable OD." to -- variable. O.D. --.

Column 8,
Line 11, change "Cut" to -- Cu --.
Line 14, change "Cut $(NO_3)_2$" to -- Cu $(NO_3)_2$ --.
Line 60, change "behaviour With" to -- behavior. With --.
Line 66, change "DNA When" to -- DNA. When --.
Line 67, change "DNTP" to -- dNTP --.

Column 9,
Line 22, change "consideration Considering" to -- consideration. Considering --.
Line 26, change "of a the" to -- of the --.
Line 63, change " Drimers" to -- primers --.
Line 65, change "[$MG^{2+}$]" to -- [$Mg^{2+}$] --.

Column 10,
Line 21, change "(B)" to -- 2.2 --.
Lines 27-28, change "The Following" to -- The Following --.
Line 37, change "variable" to -- Variable --.
Line 38, change "©" to -- 2.3 --.
Line 50, change "constant" to -- Constant --.
Line 51, change "(B)" to -- 2.2 --.
Line 54, change "or" to -- for --.

Column 11,
Line 3, change "variable" to -- Variable --.
Line 4, change "©" to -- 2.3 --.
Line 16, change "constant" to -- Constant --.
Line 17, change "(B)" to -- 2.2 --.
Line 31, change "variable" to -- Variable --.

UNITED STATES PATENT AND TRADEMARK OFFICE
CERTIFICATE OF CORRECTION

PATENT NO. : 6,277,605 B1
DATED : August 21, 2001
INVENTOR(S) : Wijnhoven et al.

It is certified that error appears in the above-identified patent and that said Letters Patent is hereby corrected as shown below:

<u>Column 11,</u>
Line 32, change "©" to -- 2.3 --.
Line 35, change -- "[$Ng^{2+}$]" to -- [$Mg^{2+}$] --

Signed and Sealed this

Twenty-eighth Day of May, 2002

Attest:

JAMES E. ROGAN
Attesting Officer     Director of the United States Patent and Trademark Office